# (12) United States Patent
Dahl et al.

(10) Patent No.: US 10,308,576 B2
(45) Date of Patent: Jun. 4, 2019

(54) METHOD FOR METHANOL SYNTHESIS

(71) Applicant: Haldor Topsøe A/S, Kgs. Lyngby (DK)

(72) Inventors: Per Juul Dahl, Vedbæk (DK); Hassan Modarresi, Lyngby (DK); Max Thorhauge, Herlev (DK)

(73) Assignee: Haldor Topsoe A/S, Lyngby (DK)

( * ) Notice: Subject to any disclaimer, the term of this patent is extended or adjusted under 35 U.S.C. 154(b) by 0 days.

(21) Appl. No.: 15/569,527

(22) PCT Filed: May 10, 2016

(86) PCT No.: PCT/EP2016/060404
§ 371 (c)(1),
(2) Date: Oct. 26, 2017

(87) PCT Pub. No.: WO2016/180812
PCT Pub. Date: Nov. 17, 2016

(65) Prior Publication Data
US 2018/0305281 A1  Oct. 25, 2018

(30) Foreign Application Priority Data
May 11, 2015 (DK) ................................ 2015 00280

(51) Int. Cl.
*C07C 29/151* (2006.01)
*C07C 31/04* (2006.01)
*B01D 3/06* (2006.01)
*B01L 3/06* (2006.01)
*C01B 3/12* (2006.01)

(52) U.S. Cl.
CPC ............ *C07C 29/1518* (2013.01); *B01L 3/06* (2013.01); *C07C 31/04* (2013.01); *B01D 2257/70* (2013.01); *C01B 3/12* (2013.01); *C01B 2203/061* (2013.01); *C01B 2203/1223* (2013.01)

(58) Field of Classification Search
CPC .... C07C 27/06; C07C 29/151; C07C 29/1516
See application file for complete search history.

(56) References Cited

U.S. PATENT DOCUMENTS

| 3,872,025 | A | | 3/1975 | Singleton |
| 3,920,717 | A | * | 11/1975 | Marion ............... C07C 29/1518 252/373 |
| 3,962,300 | A | | 6/1976 | Hiller et al. |
| 5,079,267 | A | | 1/1992 | Kao et al. |
| 5,266,281 | A | | 11/1993 | Kao et al. |
| 2009/0018220 | A1 | | 1/2009 | Fitzpatrick |

FOREIGN PATENT DOCUMENTS

WO  WO 2014/096237 A1  6/2014

* cited by examiner

*Primary Examiner* — Rosalynd A Keys
(74) *Attorney, Agent, or Firm* — Blank Rome LLP

(57) ABSTRACT

In a process for methanol production from synthesis gas, which comprises the steps of providing a make-up gas containing hydrogen and carbon monoxide, in which the content of carbon dioxide is less than 0.1 mole %, mixing the make-up gas with a hydrogen-rich recycle gas and passing the gas mixture to a methanol synthesis reactor, optionally via a sulfur guard, and subjecting the effluent from the synthesis reactor to a separation step, thereby providing crude methanol and the hydrogen-rich recycle gas, the customary addition of carbon dioxide to the make-up gas is replaced by addition of water in an amount of 0.1 to 5 mole %. This way, a $CO_2$ compressor is saved, and the amount of poisonous sulfur in the make-up gas is markedly reduced.

3 Claims, 1 Drawing Sheet

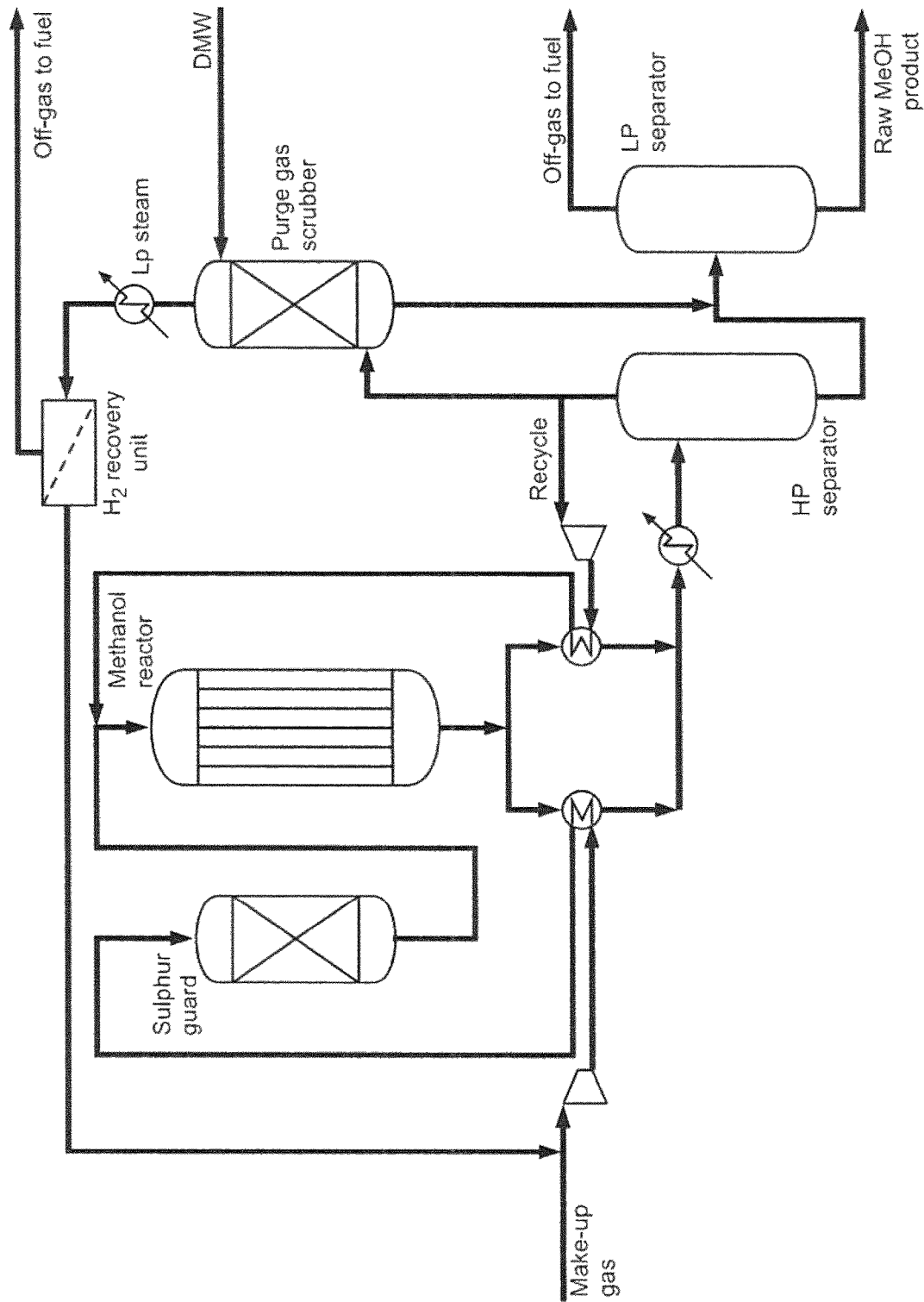

METHOD FOR METHANOL SYNTHESIS

The present invention relates to a novel method for methanol synthesis. More specifically, the invention concerns a novel treatment of the make-up gas used in a methanol synthesis loop.

Methanol is synthesized from a synthesis gas, which consists of $H_2$ and carbon oxides, i.e. CO and $CO_2$. The conversion from syngas can be formulated as a hydrogenation of either carbon monoxide or carbon dioxide, accompanied by the reverse shift reaction, and can be summarized by the following reaction sequence:

$$CO + 2H_2 <-> CH_3OH$$

$$CO_2 + 3H_2 <-> CH_3OH + H_2O$$

$$CO_2 + H_2 <-> CO + H_2O$$

The conversion is performed over a catalyst, which is most often a copper-zinc oxide catalyst on an alumina support. Examples of this catalyst include applicant's catalysts MK-121 and MK-151 FENCE™.

Producing methanol theoretically requires a synthesis gas (syngas) with a module M equal to 2. The module M is defined as $$M = (H_2 - CO_2)/(CO + CO_2).$$

As syngas typically also contains inert compounds, the optimum module may become slightly higher than 2, typically 2.05, allowing purge of the inert compounds which inevitably also will result in purge of reactants $H_2$, CO and $CO_2$. For a syngas with a module less than the optimum module as defined above, surplus carbon oxides are present, and the module must be adjusted to the required level, e.g. by recovery of $H_2$ from the purge stream and recycle of the recovered $H_2$ to the synthesis section. In known processes this is done by recovering $H_2$ from the purge in a separation unit, e.g. a PSA unit or a membrane unit, which produces a $H_2$-enriched gas for recycle and a $H_2$-depleted waste gas.

In a typical methanol production process, make-up gas is mixed with $H_2$-rich recycle gas and passed to the synthesis reactor, optionally via a sulfur guard if the make-up gas contains enough sulfur to impact the lifetime of the methanol synthesis catalyst. After mixing the make-up gas with the recycle gas, the combined gas is sent to the methanol reactor, in which hydrogen and carbon oxides react to form methanol as shown in the above reaction sequence.

Until now it has been normal practice to add $CO_2$ to the make-up gas in the methanol synthesis loop in order to maintain a sufficient selectivity of the methanol synthesis catalyst. This is because, in general, the selectivity of the methanol synthesis catalyst decreases when operating at too high $CO/CO_2$ ratios, which can be compensated for by increasing the $CO_2$ content in the make-up gas.

However, this addition of $CO_2$ to the make-up gas can be a problem, especially in coal-based methanol plants, because the $CO_2$ normally will originate from a $CO_2$ removal step, where the resulting $CO_2$ is received at ambient pressure. Moreover, this $CO_2$ will normally be contaminated with sulfur.

It has now surprisingly turned out that the problem mentioned above can be solved by adding water to the make-up gas instead of $CO_2$.

A number of prior art documents deal with the synthesis of methanol. Thus, EP 1 080 059 B1 describes a process wherein methanol is synthesized in a synthesis loop in at least two synthesis stages from a synthesis gas comprising hydrogen and carbon oxides. With said process, the problem of using a preliminary synthesis step or operating at low circulation ratios, leading to relatively high partial pressures, which in turn lead to excessive reaction and heat evolution in the catalyst bed, can be avoided.

Use of more than one methanol reactor is described in US 2010/0160694 A1, which concerns a process for the synthesis of methanol comprising passing a syngas mixture comprising a loop gas and a make-up gas through a first synthesis reactor containing a methanol synthesis catalyst to form a mixed gas containing methanol, cooling said mixed gas containing methanol and passing it through a second synthesis reactor containing a methanol synthesis catalyst, where further methanol is synthesized to form a product gas stream. This product gas stream is cooled to condense out methanol, and unreacted gas is returned as the loop gas to said first synthesis reactor. This set-up includes the use of a combination of a steam raising converter (SRC) cooled by boiling water under pressure as the first methanol reactor and a tube cooled converter (TCC) as the second methanol reactor.

The use of more than one methanol reactor is also disclosed in U.S. Pat. No. 8,629,190 B2. Synthesis gas is passed through a first, preferably water-cooled reactor, in which a part of the carbon oxides in the gas is catalytically converted to methanol, and the resulting mixture of synthesis gas and methanol vapor is supplied to a second, preferably gas-cooled reactor in series with the first reactor. In said second reactor, a further part of the carbon oxides is converted to methanol. The mixture withdrawn from the first reactor is guided through a gas/gas heat exchanger in which the mixture is cooled to a temperature below its dew point. Subsequently, methanol is separated from the gas stream and withdrawn, while the remaining gas stream is fed to the second reactor.

US 2009/0018220 A1 describes a process for synthesizing methanol, wherein a make-up gas with a stoichiometric number or module M ($M=([H_2-CO_2])/([CO_2]+[CO])$) of less than 2.0, preferably less than 1.8, is combined with unreacted synthesis gas to form a gas mixture, which is used to produce methanol in a single synthesis reactor. The make-up gas is obtained by reforming a hydrocarbon feedstock, such as methane or natural gas, and removing water from the resulting reformed gas mixture.

U.S. Pat. Nos. 5,079,267 and 5,266,281 both describe a process for the production of methanol from synthesis gas produced in a steam reformer. The synthesis gas is cooled followed by removal of $CO_2$ and $H_2O$ from the gas. Then $H_2O$ is removed to obtain a residual level of $H_2O$ of 10 ppm or lower, and $CO_2$ is removed to obtain a residual level of $CO_2$ of 500 ppm, preferably 100 ppm or lower. The synthesis gas undergoes $H_2/CO$ stoichiometric adjustment before it is sent to the methanol synthesis reactor.

Finally, U.S. Pat. No. 7,019,039 describes a high efficiency process for producing methanol from synthesis gas, wherein the stoichiometric number or module $M=([H_2-CO_2])/([CO_2]+[CO])$ of the make-up gas has been increased to about 2.05 by rejecting $CO_2$ from the gas mixture for a series of single-pass reactors.

In none of the prior art documents, the possibility of replacing the $CO_2$ addition to the make-up gas with an addition of water is suggested.

Thus, the present invention relates to a process for methanol production from synthesis gas, said process comprising the following steps:

providing a make-up gas containing hydrogen and carbon monoxide, in which the content of carbon dioxide is less than 0.1 mole %, mixing the make-up gas with a hydrogen-rich recycle gas and passing the gas mixture to a methanol synthesis reactor, optionally via a sulfur guard, and subjecting the effluent from the synthesis reactor to a separation step, thereby providing crude methanol and the hydrogen-rich recycle gas, wherein the customary addition of carbon dioxide to the make-up gas is replaced by addition of water in an amount to obtain a water content of 0.1 to 5 mole % in the make-up gas.

The amount of added water preferably corresponds to a content of 0.5 to 2.5 mole %, most preferably 0.8 to 1.2 mole % in the make-up gas.

By adding water to the make-up gas instead of adding carbon dioxide, the otherwise necessary compression of $CO_2$ is omitted and thus a $CO_2$ compressor is saved to the benefit of the process economy.

At the same time, the amount of poisonous sulfur in the make-up gas is markedly reduced.

The presence of sufficient $CO_2$ in the make-up gas is still necessary. The improvement over the prior art lies in the fact that the water addition will ensure sufficient $CO_2$ for the methanol synthesis via the shift reaction $$CO + H_2O \leftrightarrow CO_2 + H_2$$

In the following the invention will be further described with reference to the appended FIGURE, which is exemplary and not to be construed as limiting for the invention. The FIGURE shows a plant which can be used according to the present invention. The make-up gas, to which water has been added, is mixed with $H_2$-rich recycle gas and passed to the methanol reactor. From this reactor a product stream and a purge stream are withdrawn. The purge stream is heated in a preheater and mixed with the process steam to obtain a mixed stream, which is passed to a shift conversion unit, where steam and CO react to $H_2$ and $CO_2$. The reacted gas is cooled to below its dew point in a cooler. The cooled stream is passed to a process condensate separator, and the vapor stream from the condensate separator is passed to a hydrogen recovery unit. From this unit a hydrogen-enriched stream and a hydrogen-depleted waste gas stream are withdrawn. The hydrogen-enriched gas may be compressed in a recycle compressor to form the hydrogen-enriched recycle stream, which is added to the make-up gas as described above.

The invention is illustrated further in the examples 1-4, which follow. The examples illustrate four different cases with constant converter pressure drop and various make-up gas (MUG) compositions, viz.

Case 1: No $CO_2$; no $H_2O$ in MUG
Case 2: 1 mole % $CO_2$; no $H_2O$ in MUG
Case 3: No $CO_2$; 1 mole % $H_2O$ in MUG
Case 4: No $CO_2$; 2 mole % $H_2O$ in MUG The carbon loop efficiency listed in the examples is a direct measure of the methanol synthesis efficiency.

In case 1 the carbon loop efficiency is significantly lower than in cases 2 to 4. This illustrates the necessity of the presence of $CO_2$ or a $CO_2$ generator in the make-up gas. Cases 2 to 4 illustrate that $CO_2$ in the make-up gas can be replaced by $H_2O$ as it is possible to obtain similar carbon loop efficiencies.

EXAMPLE 1

This example shows the impact of the MUG composition on the synthesis loop performance in the base case: 29% CO, 67% $H_2$, 3% $N_2$ and 1% $CH_4$; no $CO_2$ and no $H_2O$ in the MUG.

The following results were found:

| Recycle ratio | 2.799 |
|---|---|
| Steam production | 3.535 kg/h |
| BWR MeOH production | 272.795 MTPD |
| LPS MeOH production | 163.873 MTPD |
| HPS MeOH production | 178.042 MTPD |
| Water content in crude MeOH | 0.82 wt % |
| Carbon loop efficiency | 11.33% |
| Carbon BWR reactor efficiency | 5.07% |
| MUG | 1.454 $Nm^3$/h |
| Recycle | 4.069 $Nm^3$/h |
| Flash | 80.410 $Nm^3$/h |
| Purge | 1.281 $Nm^3$/h |
| Total purge | 1.282 $Nm^3$/h |

Gas compositions, measured as recycle gas composition (RGC), converter inlet gas composition (CIGC) and converter outlet gas composition (COGC) were as follows:

|  | RGC | CIGC | COGC |
|---|---|---|---|
| $H_2$, mole % | 66.69 | 66.77 | 66.06 |
| CO, mole % | 28.04 | 28.29 | 27.78 |
| $CO_2$, mole % | 0.126 | 0.093 | 0.13 |
| $N_2$, mole % | 3.400 | 3.295 | 3.37 |
| $CH_4$, mole % | 1.132 | 1.097 | 1.12 |

Data for the boiling water reactor (BWR):

| Space-time yield, kg MeOH/kg catalyst/h | 0.210 |
|---|---|
| BWR inlet bed pressure, $kg/cm^2 \cdot g$ | 81.475 |
| BWR outlet bed pressure, $kg/cm^2 \cdot g$ | 79.475 |
| Pressure drop, $kg/cm^2$ | 2.00 |
| Number of tubes | 4405 |
| Total catalyst mass, kg | 5.412 |
| Duty of BWR, MW | 2.449 |

Temperatures:

| BWR temperature, ° C. | 230 |
|---|---|
| Approach temperature to MeOH equilibrium, ° C. | 179.35 |
| BWR inlet temperature, ° C. | 208.00 |
| BWR outlet temperature, ° C. | 233.55 |
| Maximum catalyst temperature (hot spot) , ° C. | 233.91 |

EXAMPLE 2

This example shows the impact of the MUG composition on the synthesis loop performance in case 2: 1 mole % $CO_2$ and no $H_2O$ in the MUG.

The following results were found:

| Recycle ratio | 2.987 |
|---|---|
| Steam production | 6.123 kg/h |
| BWR MeOH production | 1.479 MTPD |
| LPS MeOH production | 1.383 MTPD |
| HPS MeOH production | 1.426 MTPD |
| Water content in crude MeOH | 1.525 wt % |
| Carbon loop efficiency | 95.58% |
| Carbon BWR reactor efficiency | 62.62% |

| | |
|---|---|
| MUG | 1.454 Nm³/h |
| Recycle | 4.342 Nm³/h |
| Flash | 654.137 Nm³/h |
| Purge | 2.176 Nm³/h |
| Total purge | 2.241 Nm³/h |

Gas compositions, measured as RGC, CIGC and COGC were as follows:

| | RGC | CIGC | COGC |
|---|---|---|---|
| $H_2$, mole % | 67.86 | 67.65 | 62.16 |
| CO, mole % | 4.952 | 10.73 | 4.54 |
| $CO_2$, mole % | 1.191 | 1.143 | 1.12 |
| $N_2$, mole % | 19.334 | 15.237 | 17.72 |
| $CH_4$, mole % | 6.044 | 4.779 | 5.56 |

Data for the boiling water reactor (BWR):

| | |
|---|---|
| Space-time yield, kg MeOH/kg catalyst/h | 1.139 |
| BWR inlet bed pressure, kg/cm² · g | 81.475 |
| BWR outlet bed pressure, kg/cm² · g | 79.475 |
| Pressure drop, kg/cm² | 2.00 |
| Number of tubes | 4405 |
| Total catalyst mass, kg | 5.412 |
| Duty of BWR, MW | 42.449 |

Temperatures:

| | |
|---|---|
| BWR temperature, ° C. | 230 |
| Approach temperature to MeOH equilibrium, ° C. | 49.67 |
| BWR inlet temperature, ° C. | 208.00 |
| BWR outlet temperature, ° C. | 240.95 |
| Maximum catalyst temperature (hot spot), ° C. | 247.85 |

EXAMPLE 3

This example shows the impact of the MUG composition on the synthesis loop performance in case 3: No $CO_2$ and 1 mole % $H_2O$ in the MUG.

The following results were found:

| | |
|---|---|
| Recycle ratio | 3.175 |
| Steam production | 5.886 kg/h |
| BWR MeOH production | 1.429 MTPD |
| LPS MeOH production | 1.326 MTPD |
| HPS MeOH production | 1.366 MTPD |
| Water content in crude MeOH | 1.606 wt % |
| Carbon loop efficiency | 94.96% |
| Carbon BWR reactor efficiency | 61.69% |
| MUG | 1.454 Nm³/h |
| Recycle | 4.617 Nm³/h |
| Flash | 594.468 Nm³/h |
| Purge | 2.677 Nm³/h |
| Total purge | 2.737 Nm³/h |

Gas compositions, measured as RGC, CIGC and COGC were as follows:

| | RGC | CIGC | COGC |
|---|---|---|---|
| $H_2$, mole % | 72.71 | 71.35 | 67.20 |
| CO, mole % | 4.815 | 10.37 | 4.45 |
| $CO_2$, mole % | 0.996 | 0.757 | 0.94 |
| $N_2$, mole % | 15.838 | 12.763 | 14.64 |
| $CH_4$, mole % | 5.019 | 4.057 | 4.65 |

Data for the boiling water reactor (BWR):

| | |
|---|---|
| Space-time yield, kg MeOH/kg catalyst/h | 1.101 |
| BWR inlet bed pressure, kg/cm² · g | 81.475 |
| BWR outlet bed pressure, kg/cm² · g | 79.475 |
| Pressure drop, kg/cm² | 2.00 |
| Number of tubes | 4405 |
| Total catalyst mass, kg | 5.412 |
| Duty of BWR, MW | 40.778 |

Temperatures:

| | |
|---|---|
| BWR temperature, ° C. | 230 |
| Approach temperature to MeOH equilibrium, ° C. | 58.97 |
| BWR inlet temperature, ° C. | 208.00 |
| BWR outlet temperature, ° C. | 240.70 |
| Maximum catalyst temperature (hot spot), ° C. | 245.90 |

EXAMPLE 4

This example shows the impact of the MUG composition on the synthesis loop performance in case 4: No $CO_2$ and 2 mole % $H_2O$ in the MUG.

The following results were found:

| | |
|---|---|
| Recycle ratio | 3.339 |
| Steam production | 5.813 kg/h |
| BWR MeOH production | 1.408 MTPD |
| LPS MeOH production | 1.303 MTPD |
| HPS MeOH production | 1.365 MTPD |
| Water content in crude MeOH | 3.523 wt % |
| Carbon loop efficiency | 96.75% |
| Carbon BWR reactor efficiency | 74.78% |
| MUG | 1.454 Nm³/h |
| Recycle | 4.854 Nm³/h |
| Flash | 538.024 Nm³/h |
| Purge | 2.773 Nm³/h |
| Total purge | 2.827 Nm³/h |

Gas compositions, measured as RGC, CIGC and COGC were as follows:

| | RGC | CIGC | COGC |
|---|---|---|---|
| $H_2$, mole % | 75.94 | 73.88 | 70.36 |
| CO, mole % | 2.098 | 7.84 | 1.95 |
| $CO_2$, mole % | 1.121 | 0.863 | 1.06 |
| $N_2$, mole % | 15.341 | 12.497 | 14.22 |
| $CH_4$, mole % | 4.894 | 3.997 | 4.55 |

Data for the boiling water reactor (BWR):

| | |
|---|---|
| Space-time yield, kg MeOH/kg catalyst/h | 1.084 |
| BWR inlet bed pressure, kg/cm² · g | 81.475 |
| BWR outlet bed pressure, kg/cm² · g | 79.475 |
| Pressure drop, kg/cm² | 2.00 |
| Number of tubes | 4405 |
| Total catalyst mass, kg | 5.412 |
| Duty of BWR, MW | 40.270 |

Temperatures:

| | |
|---|---|
| BWR temperature, ° C. | 230 |
| Approach temperature to MeOH equilibrium, ° C. | 44.05 |
| BWR inlet temperature, ° C. | 208.00 |
| BWR outlet temperature, ° C. | 237.36 |
| Maximum catalyst temperature (hot spot), ° C. | 246.67 |

The invention claimed is:

1. A process for methanol production from synthesis gas, said process comprising the following steps:
provding a make-up gas containing hydrogen and carbon monoxide, in which the content of carbon dioxide is less than 0.1 mole %,
mixing the make-up gas with a hydrogen-rich recycle gas and passing the gas mixture to a methanol synthesis reactor, optionally via a sulfur guard, and
subjecting the effluent from the synthesis reactor to a separation step, thereby providing crude methanol and the hydrogen-rich recycle gas,
wherein the customary addition of carbon dioxide to the make-up gas is replaced by addition of water to the make-up gas in an amount to obtain a water content of 0.1 to 5 mole % in the make-up gas which is mixed with the hydrogen-rich recycle gas and passed to the methanol synthesis reactor.

2. Process according to claim 1, wherein the amount of added water corresponds to a content of 0.5 to 2.5 mole % in the make-up gas.

3. Process according to claim 2, wherein the amount of added water corresponds to a content of 0.8 to 1.2 mole % in the make-up gas.

* * * * *